United States Patent
Blomqvist et al.

(10) Patent No.: US 9,522,275 B2
(45) Date of Patent: Dec. 20, 2016

(54) METHODS AND SYSTEMS FOR STIMULATING A HEART

(75) Inventors: Andreas Blomqvist, Taby (SE); Torbjorn Persson, Malmo (SE); Rolf Hill, Jarfalla (SE)

(73) Assignee: St. Jude Medical AB, Jarfalla (SE)

( * ) Notice: Subject to any disclaimer, the term of this patent is extended or adjusted under 35 U.S.C. 154(b) by 9 days.

(21) Appl. No.: 13/884,934

(22) PCT Filed: Nov. 30, 2010

(86) PCT No.: PCT/EP2010/068472
§ 371 (c)(1),
(2), (4) Date: May 10, 2013

(87) PCT Pub. No.: WO2012/072104
PCT Pub. Date: Jun. 7, 2012

(65) Prior Publication Data
US 2013/0238045 A1 Sep. 12, 2013

(51) Int. Cl.
*A61N 1/365* (2006.01)
*A61N 1/362* (2006.01)
*A61N 1/368* (2006.01)

(52) U.S. Cl.
CPC .......... *A61N 1/365* (2013.01); *A61N 1/3627* (2013.01); *A61N 1/3682* (2013.01); *A61N 1/3684* (2013.01); *A61N 1/36585* (2013.01)

(58) Field of Classification Search
CPC  A61N 1/365; A61N 1/36585; A61N 1/36514; A61N 1/36564; A61N 1/36571; A61N 1/36578; A61N 1/3684; A61N 1/3682; A61N 1/3627
See application file for complete search history.

(56) References Cited

U.S. PATENT DOCUMENTS

| 5,700,283 | A | 12/1997 | Salo |
| 7,558,627 | B1 * | 7/2009 | Turcott ........................... 607/27 |
| 2006/0241703 | A1 | 10/2006 | Ding et al. |
| 2007/0179541 | A1 | 8/2007 | Prakash et al. |
| 2008/0103539 | A1 | 5/2008 | Stegemann et al. |
| 2009/0018597 | A1 * | 1/2009 | Wenzel .................. A61N 1/365 607/23 |

(Continued)

OTHER PUBLICATIONS

International Search Report—Int'l App No. PCT/EP2010/068472; Int'l Filing Date: Nov. 30, 2010.

(Continued)

*Primary Examiner* — Michael Kahelin (57) ABSTRACT

Methods and systems for optimizing stimulation of a heart of a patient are disclosed. The method comprises: determining recommended pacing settings including recommended AV delays and/or recommended VV delays based on IEGM data. Further, at least one hemodynamical parameter is determined based on measured at least one hemodynamical signal. Reference pacing settings are determined including reference AV delays and/or reference VV delays based on said hemodynamical parameters. An AV delay correction value and a VV delay correction value are calculated as a difference between recommended AV and/or VV delays and reference AV and/or VV delays, respectively. The correction values are used for updating recommended AV and/or VV delays, respectively.

17 Claims, 5 Drawing Sheets

(56) References Cited

U.S. PATENT DOCUMENTS

2010/0106212 A1    4/2010  Hedberg et al.
2010/0145405 A1    6/2010  Min et al.

OTHER PUBLICATIONS

Written Opinion of the Int'l Searching Authority—Int'l App. No. PCTEP2010/068472; Int'l Filing Date: Nov. 30, 2010.

Abraham, William T. MD et al., "Rationale and design of a randomized clinical trial to assess the safety and efficacy of frequent optimization of cardiac resynchronization therapy: The Frequent Optimization Study Using the QuickOpt Method (FREEDOM) Trial," Am Heart J. 2010;159:944-948.e1.

Gras, Daniel MD, "Optimization of AV and VV Delays in the Real-World CRT Patient Population: an International Survey on Current Clinical Practice," PACE. 2009;32:S236-S239.

Kamdar, Ravindu et al., "A prospective comparison of echocardiography and device algorithms for atrioventricular and interventricular interval optimization in cardiac sychronization therapy," Europace. 2010;12:34-91.

Strauss, Margit et al., Impact of moderate exercise workload on predicted optimal AV and VV delays determined by an intracardiac electrogram-based method for optimizing cardiac resynchronization therapy., Clin Res Cardiol. 2010;99:734-741.

Van Gelder, Berry M. Ph.D et al., "The Optimized V-V Interval Determined by Interventricular Conduction Times Versus Invasive Measurement by LVdP/dt max," J Cardiovasc Electrophysiol. 2008;19:939-944.

\* cited by examiner

METHODS AND SYSTEMS FOR STIMULATING A HEART

CROSS REFERENCE TO RELATED APPLICATION(S)

This is a U.S. national stage application of International Application No. PCT/EP2010/068472, filed on Nov. 30, 2010.

FIELD OF THE INVENTION

The present invention relates generally to methods and for implantable medical devices and systems including such devices and more particularly to methods and systems for optimizing stimulation of a heart of a patient.

BACKGROUND OF THE INVENTION

Heart failure is usually a chronic, long term condition, but may occur suddenly. It may affect the left heart, the right heart, or both sides of the heart. Heart failure may be considered as a cumulative consequence of all injuries and/or stress to the heart over a person's life and the prevalence of heart failure increases constantly. For example, it is estimated that nearly 5 million people in the U.S.A. suffer from heart failure and about 400.000 new cases are diagnosed every year. The prevalence of heart failure approximately doubles with each decade of life. One of the most important means of treating heart failure is cardiac resynchronization therapy, CRT. Although CRT is a very effective way of treating heart failure in most patients there is a large percentage for which the CRT has no apparent effect at all. Different estimates of the size of the so called group "non-responders" exist, but it is generally believed to be in the vicinity of 25% of all patients provided with a CRT device. However, there are numbers reported to be as high as 33% (depending mostly on the definition of CRT response which may vary greatly).

A common method for adapting the CRT (the timing cycles) for non-responders is so called echo-based optimization, which may include M-mode, 2D, 3D and TDI. Echo-based optimization of the timing cycles is often time-consuming and may range from 30 minutes to two hours depending on the scope of the evaluation. Furthermore, echo-based optimization is heavily dependent of the operator, who interprets the displayed echo signals, for accuracy and consistency. Accordingly, there is a need for more reliable, fast, and accurate methods for CRT timing optimization and for patient customized CRT timing optimization.

Device based CRT optimization is likely to be one of the most potent tools in improving CRT efficiency and more specifically fighting non-responders. St. Jude Medical's QuickOpt™ Timing Cycle Optimization is an algorithm that provides IEGM (Intracardiac Electrogram) based AV (Atrial-Ventricular) timing optimization in CRT and ICD (Implantable Cardioverter-Defibrillator) systems and VV (Ventricular-Ventricular) timing optimization in CRT devices in a simple and swift way. QuickOpt™ Timing Cycle Optimization is based on the hypothesis that the point of time for the closure of the Mitral valve can be estimated by measuring the interatrial conduction time (P-wave duration), that the onset of isovolumetric contraction can be measured using the peak of the R-wave and that interventricular conduction delays can be measured by evaluating simultaneous RV (Right Ventricular) and LV (Left Ventricular) IEGMs and measuring the time between the peaks of the R-waves. The goal is to characterize interatrial conduction patterns so that preload is maximized and ventricular pacing does not occur until after full closure of the mitral valve and to characterize intrinsic and paced interventricular conduction patterns so that pacing stimuli and the resultant LV and RV conduction (paced wave fronts) meet at the ventricular septum. Accordingly, QuickOpt™ Timing Cycle Optimization electrically characterizes the conduction properties of the heart to calculate optimal paced and sensed AV delay, i.e. the time interval between a paced atrial event and the ventricular impulse and a sensed atrial event and the ventricular impulse, respectively, and/or VV delay. QuickOpt™ Timing Cycle Optimization has been clinically proven to correlate with the more time-consuming echo-based methods and may be used for patients carrying CRT and dual-chamber devices at implant or follow up. QuickOpt™ Timing Cycle Optimization is an appealing optimization method since it does not require systematic measurements of a number of different AV and VV delays, which makes it very fast and simple. There are other IEGM based optimization methods among which QuickOpt™ Timing Cycle Optimization is one such method.

Despite the evident advantages of IEGM based optimization methods, such as e.g. QuickOpt™ Timing Cycle Optimization, there is an opinion within the medical community, for example, among physicians that results, e.g. timing cycles, based on input data more directly reflecting the mechanical functioning of the heart may be even more accurate and reliable.

Thus, there is still a need within the art for further improved method and devices for optimizing AV and VV delays.

SUMMARY OF THE INVENTION

In the context of the present application, the term "paced AV delay" refers to the time interval between a paced atrial event and the ventricular impulse and the term "sensed AV delay" refers to the time interval between a sensed atrial event and the ventricular impulse. Hereinafter, the term "AV delay" will be used as including both paced AV delay and sensed AV delay if not explicitly mentioned sensed or paced AV delay.

According to an aspect of the present invention, there is provided a method for determining a delivery of cardiac pacing therapy using a cardiac stimulator and non-implantable equipment capable of measuring hemodynamical signals of the patient. The method comprises the following steps, not necessarily performed in the below given order:

a) determining recommended pacing settings including recommended paced and sensed atrio-ventricular pacing delays, AV delay and/or recommended interventricular pacing delays, VV delay, for use in the cardiac pacing therapy based on IEGM data;

b) measuring at least one hemodynamical signal of the patient using the non-implantable equipment;

c) determining at least one hemodynamical parameter based on the at least one hemodynamical signal;

d) determining reference pacing settings including reference paced and sensed atrio-ventricular pacing delays, AV delay and/or reference interventricular pacing delays, VV delay, based on optimized hemodynamical parameters;

e) calculating an AV delay correction value as a difference between a recommended AV delay and a reference AV delay, and/or a VV delay correction value as a difference between a recommended VV delay and a reference VV delay; and f) updating the recommended AV and/or VV delay with the AV and/or VV delay correction value, respectively, to obtain a modified recommended AV and/or VV delay.

According to a further aspect of the present invention there is provided a system including a cardiac stimulator, and non-implantable equipment capable of measuring hemodynamical signals of the patient, wherein the non-implantable equipment is configured to determine at least one hemodynamical parameter based on at least one measured hemodynamical signal. The system further comprises:

an optimization module configured to determine recommended pacing settings including recommended atrio-ventricular pacing delays, AV delay and/or recommended interventricular pacing delays, VV delay, based on IEGM data;

a reference setting determining module configured to determine reference pacing settings including reference atrio-ventricular pacing delays, AV delay and/or reference interventricular pacing delays, VV delay, based on the hemodynamical parameters;

a calculation module configured to calculate an AV delay correction value as a difference between a recommended AV delay and a reference AV delay, and/or a VV delay correction value as a difference between a recommended VV delay and a reference VV delay; and an updating module configured to instruct a pacing module to use the AV and/or VV delay correction value in cardiac resynchronization therapy and/or optimization of AV and/or VV delays.

According to an embodiment of the system, an extracorporeal programmer unit capable of communicating with the cardiac stimulator implanted in the patient and with the non-implantable equipment is also included.

The present invention is based on the insight that an IEGM based optimization of timing cycles, such as Quick-Opt™ Timing Cycle Optimization, can be further improved by using patient specific correction values created by means of one or several hemodynamical parameters reflecting the mechanical functioning of the heart of that particular patient at different AV and/or VV delays. The one or several hemodynamical parameters are determined based on hemodynamical signals gathered by means of non-implantable equipment, including for example extracorporeal equipment such as a programmer device or catheter-based equipment that is wholly or partly invasive, operating on the particular patient, for example, at a follow-up visit at the clinic. Several hemodynamical parameters using one or more different types of equipment can be used to create the patient specific correction values.

That is, QuickOpt™ Timing Cycle Optimization can be improved and customized to particular needs of a specific patient using an external reference to train the QuickOpt™ Timing Cycle Optimization for that specific patient.

QuickOpt™ Timing Cycle Optimization is based on the hypothesis that the point of time for mitral valve closure can be estimated by measuring the interatrial conduction time (P-wave duration), that onset of isovolumetric contraction can be measured using the peak of the R-wave, and that interventricular conduction delays can be measured by evaluating simultaneous RV and LV IEGM:s and measuring the time between peaks of the R-waves.

Because the AV and VV delays calculated using IEGM based optimization such as QuickOpt™ Timing Cycle Optimization are partly based on a hypothetical foundation, the inventors have arrived at the insight that the AV and VV delays can be made more accurate and patient specific by using correction parameters based on patient specific hemodynamical signals, which directly reflects the mechanical functioning of the heart, obtained by means of non-implantable equipment, including for example non-invasive equipment such as echocardiography/ultrasound equipment or invasive catheter-based equipment such as catheter based equipment for measuring pulmonary capillary wedge pressure (left atrial pressure surrogate) or a Swan-Ganz catheter.

In fact, the optimization can be improved in a number of different ways by updating and modifying the AV and VV delays based on parameters calculated using reference AV and VV delays based on hemodynamical data obtained by means of non-implantable equipment. Studies have shown that AV and VV delays based on hemodynamical signals may be more reliable and accurate than IEGM based delays. For example, there are studies showing a poor correlation between IEGM based delays and delays based on pressure measurements, e.g. LV $dP/dt_{max}$, ("The Optimized V-V interval Determined by Interventricular Conduction Times versus Invasive Measurement by LV dP/dtmax", van Gelder, et al.). Hence, the reliability and accuracy of the AV and VV delays, and thus the CRT, can be improved using the combined IEGM and hemodynamical based optimization as suggested by the present invention. Furthermore, the IEGM based optimizations, such as e.g. QuickOpt™ Timing Cycle Optimization, may not deliver the optimal AV and VV delays for all patients due to the fact that they are to some extent based on a hypothesis created from average values and parameters collected from a large number of patients. Thereby, there might be individual patients for whom the IEGM based AV and VV delays are not suitable or less optimal. By adapting and tailoring the IEGM based delays with data from the hemodynamical measurements obtained from the specific patient after implantation, better AV and VV delays adapted for that specific patient can be created.

An example procedure using the present invention to improve IEGM based AV and/or VV delays using an external reference can be performed as follows. At a clinic, e.g. during a follow-up visit for a patient carrying an implanted cardiac stimulator, an optimization of the AV and/or VV delay using external non-implantable equipment is performed preferably under supervision. The non-implantable equipment may, for example, include echocardiographic equipment, finger photoplethysmographic equipment, equipment for measuring trans-thoracic impedance, or equipment for measuring heart sounds. Based on hemodynamical signals obtained by means of this non-implantable equipment, optimal AV and/or VV delays are determined, or reference AV and/or VV delays. In connection to this step, before or after, recommended AV and/or VV delays are determined using an IEGM based optimization, preferably QuickOpt™. Difference values are determined between the reference delays and the recommended delays or correction values. The correction values are used to update or modify recommended delays.

In subsequent optimization procedures, IEGM based optimizations are performed, which e.g. may be initiated automatically by the implanted cardiac stimulator itself or by the physician at the clinic, to obtain new AV and/or VV delays. The new set of AV and/or VV delays are updated with correction values, which are determined in each optimization procedure by comparing a new set of AV and/or VV delays with a reference set of AV and/or VV delays, either the reference set of AV and/or VV delays from the initial optimization session or a new reference set of AV and/or VV delays. The new correction values may, in turn, also be modified or updated in each optimization procedure using older correction values (i.e. correction values created in an earlier optimization procedure), i.e. by adding the new (and likely smaller) correction value to the older or previous one. Thereby, as time progresses, this will lead to that the correction values will diminish and asymptotically approach a certain value.

According to some embodiments of the present invention, an approximate heart rate or heart rate range is associated with or labeled to each AV or VV correction parameter. The AV and VV delay correction values may be binned together according to what approximate heart rate or heart rate range at which the AV and/or VV delays used for the calculation of the correction values were acquired. Thereby, it is possible to obtain heart rate specific correction values and, in turn, optimized heart rate specific AV and VV delays and thus it is possible to obtain rate dependent correction values and optimized rate dependent AV and VV delays. Further, interpolation and/or extrapolation of the relationship between the correction values and heart rate and/or heart rate range can be used to predict appropriate correction values for a heart rate and/or heart rate range at which no data yet has been collected.

According to an embodiment of the present invention, the reference AV and/or VV delays obtained in an optimization procedure including an optimization session for finding reference AV and/or VV delays and an optimization session for finding recommended AV and/or VV delays are temporarily used in pacing therapy during a period of time between a optimization procedure and a subsequent optimization procedure.

According to embodiments of the present invention, the non-implantable equipment is any one from the group including: non-invasive echocardiography/ultrasound equipment, non-invasive heart sound equipment, non-invasive photoplethysmography equipment for measurement using the fingers of the patient, non-invasive magnetic resonance imaging (MRI) equipment, a swan-Ganz catheter: catheter based equipment for measuring pulmonary capillary wedge pressure (left atrial pressure surrogate, or a Millar catheter or pressure wire for measuring left ventricular pressure.

In embodiments of the present invention, the at least one hemodynamical parameter is a parameter, or combination of parameters, from the group including: stroke volume (SV), cardiac output (CO), ejection fraction (EF), trans mitral flow, septal to lateral wall activation delay, the first heart sound (S1), the second heart sound (S2), the energy of the first or second heart sound, LV $dP/dt_{max}$, pulmonary capillary wedge pressure, and/or left ventricual pressure.

In embodiments of the present invention, the calculation module is arranged in the programmer unit or the cardiac stimulator.

According to embodiments of the present invention, the optimization module is arranged in the programmer unit or the cardiac stimulator.

In embodiments of the present invention, the reference setting determining module is arranged in the programmer unit or in the non-implantable equipment.

According to embodiments of the present invention, the updating module is arranged in the programmer unit or the cardiac stimulator.

Further objects and advantages of the present invention will be discussed below by means of exemplifying embodiments.

These and other features, aspects and advantages of the invention will be more fully understood when considered with respect to the following detailed description, appended claims and accompanying drawings.

BRIEF DESCRIPTION OF THE DRAWINGS

Exemplifying embodiments of the invention are illustrated by way of example and not by way of limitation in the figures of the accompanying drawings in which like references indicate similar elements. It should be noted that references to "an" or "one" embodiment in this discussion are not necessarily to the same embodiment, and such references mean at least one.

DESCRIPTION OF EXEMPLIFYING EMBODIMENTS

The following is a description of exemplifying embodiments in accordance with the present invention. This description is not to be taken in limiting sense, but is made merely for the purposes of describing the general principles of the invention. It is to be understood that other embodiments may be utilized and structural and logical changes may be made without departing from the scope of the present invention.

Figure 1:
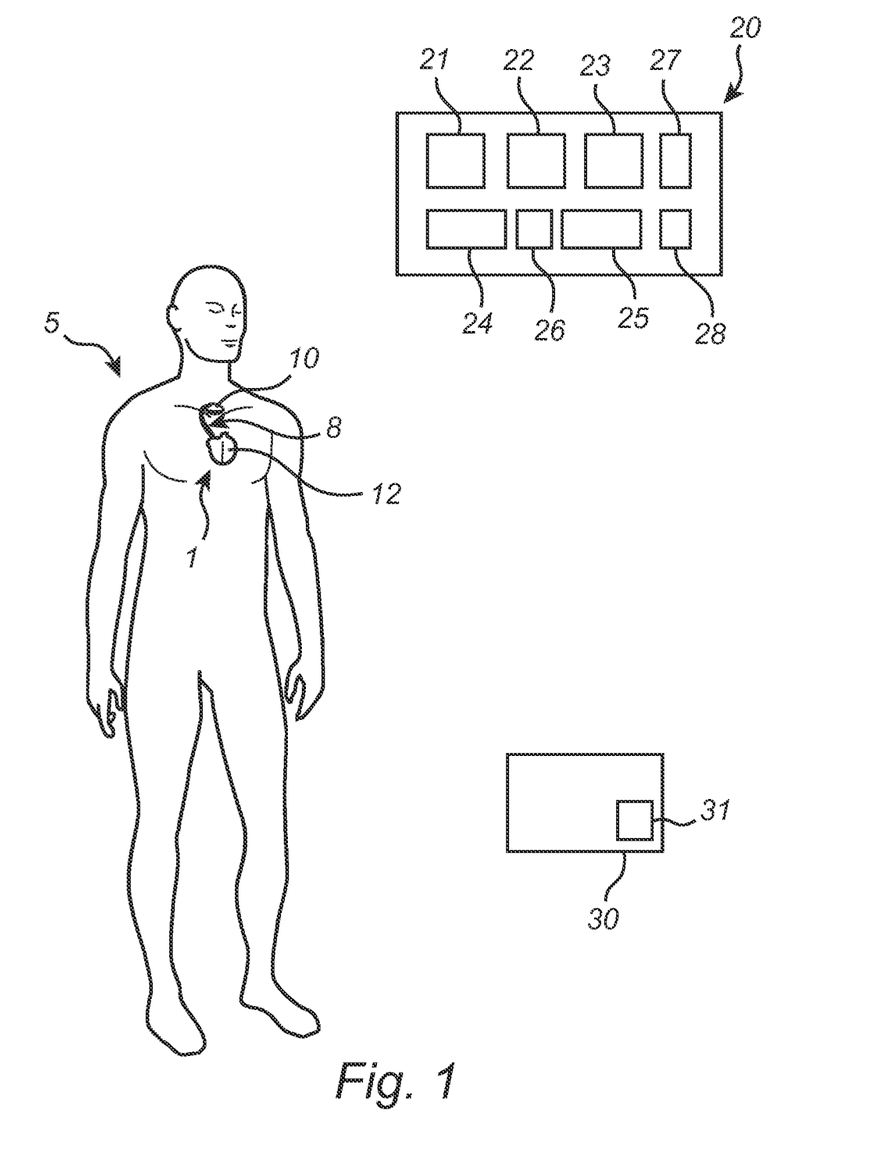
FIG. 1 is a schematical diagram illustrating a system in which the method according to the present invention can be implemented.

Referring to FIG. 1, a system environment in which the method according to the present invention may be implemented will be described. The method is briefly described with reference to FIG. 1 but will be described in more detail with reference to FIGS. 3-5. An initial session to determine optimal AV and/or VV delays can be performed, for example, at a follow-up visit by a patient 5 carrying an implanted cardiac stimulator 10 at a clinic. Preferably, such an initial optimization session is performed under supervision of a physician. The cardiac stimulator 10 may include an optimization module 48 (see FIG. 2) configured to determine recommended pacing settings including recommended sensed and paced atrio-ventricular pacing delays, AV delay and/or recommended interventricular pacing delays, VV delay, for use in, for example, cardiac resynchronization therapy based on IEGM data. Preferably, the optimization module 48 is configured to determine recommended AV and/or VV delays using QuickOpt™. The cardiac stimulator 10 is connectable to one or more medical leads 8. The implantable cardiac stimulator 10 can thereby be set in electrical communication with the patient's heart 1 by way of the leads 8, for example, suitable for delivering multichamber stimulation therapy.

Furthermore, the cardiac stimulator 10 is configured to communicate with extracorporeal equipment, such as a programmer unit or workstation 20. The programmer unit 20 comprises a control unit 21, a memory unit 22, communication unit (e.g. a telemetry unit) 23, and a display unit 24. In an alternative embodiment, the programmer unit 20 may also include an optimization module 25 configured to determine recommended pacing settings including recommended atrio-ventricular pacing delays, AV delay and/or recommended interventricular pacing delays, VV delay, for use in, for example, cardiac pacing therapy based on IEGM data.

An optimization session to determine recommended AV and/or VV delays may be initiated automatically by the cardiac stimulator 10 or the programmer unit 20, or manually by a physician via the programmer unit 20.

Furthermore, non-implantable equipment 30 capable of measuring hemodynamical signals of the heart 1 of the patient 5 is configured to communicate with the programmer unit 20 and, optionally, to the cardiac stimulator 10, e.g. wirelessly using telemetry. The non-implantable equipment 30 is not intended for chronic implantation and may include at least one or a combination of the equipment presented below. The list of example equipment given below is non-exhaustive. Further, examples of hemodynamical signals measured with respective equipment are also given together with examples of hemodynamical parameters that may be used in an optimization of AV and/or VV delays:

non-invasive echocardiography/ultrasound equipment: This equipment may be based on ultrasound crystals generating pulses from a hand held probe that reflects tissue properties. By automatically moving the ultrasound beam, a 2D picture can be produced from which parameters can be derived. Examples of such parameters includes
Aortic velocity time integral (correlates with stroke volume (SV))
Trans mitral flow which can be used for AV optimization by studying the A- and E-waves and their relationship.
Intra- and inter ventricular dyssynchrony for VV-optimization (e.g. septal to lateral wall activation delay)

Non-invasive heart sound equipment: This equipment can measure the sound produced by valve closures and contractions against closed valves (e.g. S1 and S2). The timing data of, or power or energy of S1 and/or S2 can for example be used to optimize the AV and/or VV delay.

Non-invasive equipment for measurement using the fingers of the patient: This equipment may include a finger-cuff photoplethysmography technique. Using this technique, for example, stroke volume and LV $dP/dt_{max}$ can be obtained and be used to optimize AV and/or VV delays.

Non-invasive magnetic resonance imaging (MRI): This technique uses a magnetic field to align the nuclear magnetization of hydrogen atoms in water in the body. Moving pictures are produced that can be quantified in same way as echocardiography images to quantify dyssynchrony or ejection-fraction or stroke volume.

Swan-Ganz catheter: This technique measures cardiac output by monitoring temperature changes after bolus injection of a cold liquid. The injection is made into a proximal port of a catheter containing a thermistor mounted at the tip, which normally is placed in the pulmonary artery. The thermistor measures the sequential changes in temperature over time. The cardiac output is inversely related to the area under a plotted curve over the thermodilution. This is a standard method for monitoring cardiac output. Based on the measured cardiac output, stroke volume can be determined by dividing the cardiac output with heart rate. The stroke volume can then be used to optimize the AV and/or VV delays.

Catheter based equipment for measuring pulmonary capillary wedge pressure (left atrial pressure surrogate): Often a balloon-tipped, multi-lumen catheter (Swan-Ganz catheter) is inserted into a peripheral vein, advanced into right atrium, right ventricle, pulmonary artery and into a branch of the pulmonary artery. Behind the tip of the catheter, a small balloon is arrange, which may be inflated with air. The catheter has a first port at the distal tip and a second part placed more proximally relative to the balloon. The ports are connected to pressure transducers. When placed in a branch of the pulmonary artery, the distal port measures pulmonary artery pressure and the proximal port measures right atrial pressure. The balloon is then inflated, which occludes the branch of the pulmonary artery. When this occurs, the pressure in the distal port rapidly falls, and after a period of time, reaches a stable lower level that is similar to the left atrial pressure. Thereafter, the balloon is deflated. This catheter can also be used to measure cardiac output.

Millar catheter or Radi pressure wire for measuring left ventricular pressure: For example, the left ventricular pressure can be measured by catheterization of the left ventricle e.g. through the femoral artery and a retrograde aortic valve. Using the left ventricle pressure signals, LV $dP/dt_{max}$ can be achieved. In order to optimize AV and/or VV delays, LV $dP/dt_{max}$ can be maximized.

Equipment for acoustic cardiography: For AV and VV delay optimization it is conceivable to use, for example, electromechanical activation time (EMAT).

Equipment for impedance cardiography: For AV and VV delay optimization it is conceivable to use, for example, stroke volume (SV) or cardiac output (CO).

Equipment for radionuclide ventriculography: For AV and VV delay optimization it is conceivable to use, for example, left ventricular ejection fraction (LVEF).

Equipment for surface ECG: For VV delay optimization it is conceivable to use, for example, QRS duration.

The non-implantable equipment 30 is used to measure at least one hemodynamical signal reflecting the mechanical work of the heart 1 and based on these hemodynamical signals at least one hemodynamical parameter can be determined, which can be performed in the non-implantable equipment 30 or in the programmer unit 20 in accordance with techniques well known in the art. A reference optimization session is executed to determine AV and/or VV delays based on these hemodynamical signals/parameters, which optimization session also may be performed in a reference setting determining module 31 of the non-implantable equipment 30 or a reference setting determining module 27 in the programmer unit 20. This can be executed by performing a scan over a set of AV and VV delays and identifying the AV and/or VV delay providing the optimal hemodynamical parameter, e.g. the maximum stroke volume. For example, a maximum AV and VV delay and a minimum AV and VV delay can be scanned to find the optimal AV and/or V delay. Often, a set of AV and/or VV delays between the maximum and minimum AV and/or VV delays are also scanned in an optimization procedure.

The programmer unit 20 may be configured to calculate correction values based on the recommended and reference AV and/or VV delays in a calculation module 26. For example, the correction values can be calculated as a difference between a recommended AV delay and a reference AV delay, and/or as a difference between a recommended VV delay and a reference VV delay. The correction values can be used to update the recommended AV and/or VV delay to obtain a modified recommended AV and/or VV delay using an updating module 28, which updated recommended Av and/or VV delays can be communicated to the cardiac stimulator 10. In an alternative embodiment, a calculation module of the cardiac stimulator 10 may be configured to calculate correction values and an updating module 65 may be configured to update the recommended delays.

In an embodiment of the present invention, the functions performed in the programmer unit 20 can be a performed in the non-implantable equipment 30, which thus may comprise a control unit, a memory unit, communication unit (e.g. a telemetry unit), and a display unit, and an optimization module 25 configured to determine recommended pacing settings including recommended atrio-ventricular pacing delays, AV delay and/or recommended interventricular pacing delays, VV delay, for use in, for example, cardiac pacing therapy based on IEGM data.

Figure 2:
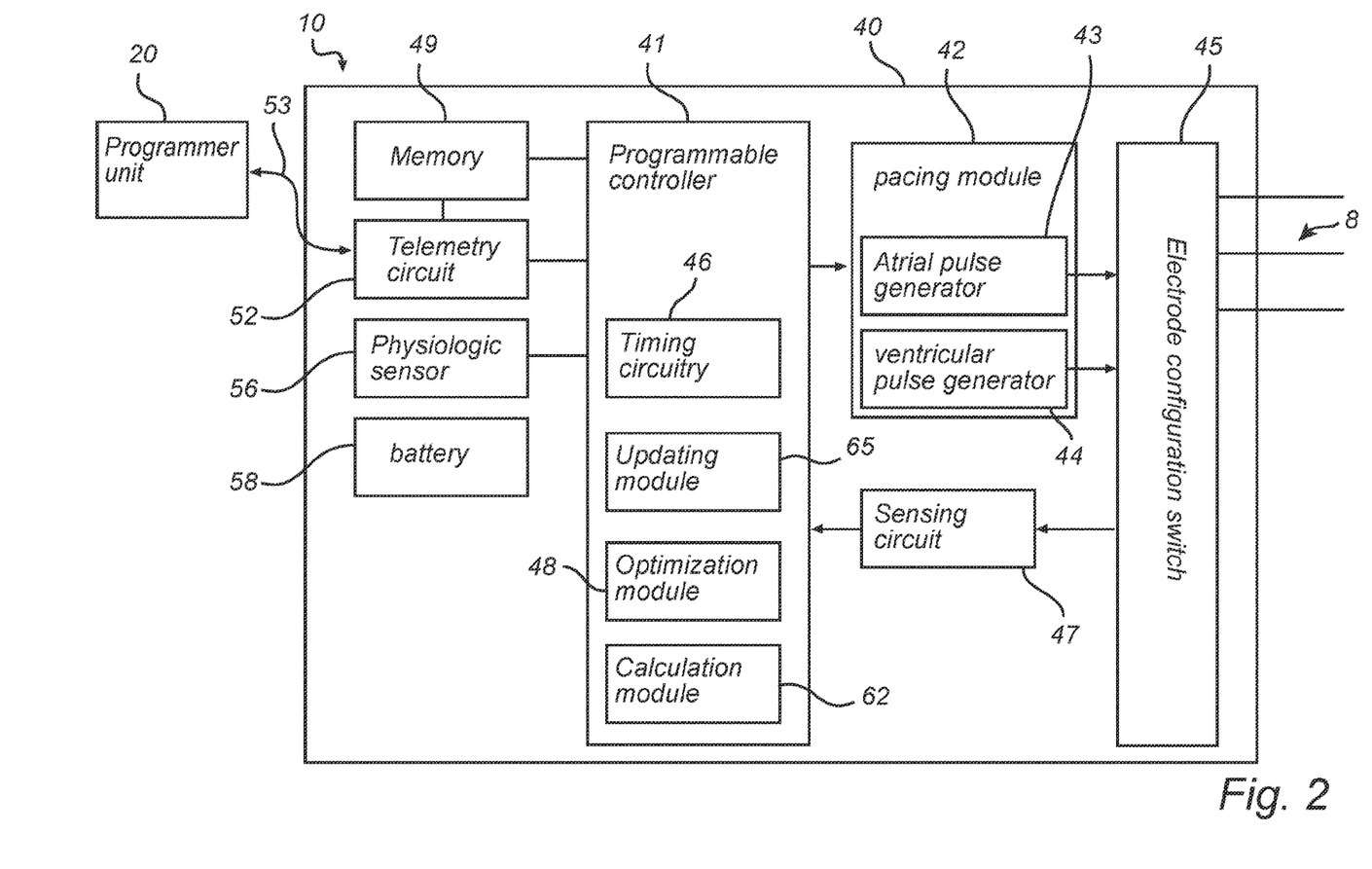
FIG. 2 is a simplified functional block diagram of one embodiment of a cardiac stimulator that can be incorporated into the system of FIG. 1.

In FIG. 2, an exemplary, simplified block diagram depicting various components of the cardiac stimulator according to embodiments of the present invention is shown. The cardiac stimulator 10 is capable of delivering cardiac resynchronization therapy and is configured to integrate both monitoring and therapy features, as will be described below. The cardiac stimulator 10 collects and processes data about the heart 12 from one or more sensors. Further, the cardiac stimulator 10 collects and processes data about the heart 12 from electrode pairs for sensing cardiac electrogram (EGM) signals. While a particular multi-chamber device is shown, it is to be appreciated and understood that this is done for illustration purposes only. Thus, the techniques and methods described below can be implemented in connection with any suitable configured or configurable stimulation device. Accordingly, one of skill in the art could readily duplicate, eliminate, or disable the appropriate circuitry in any desired combination to provide a device capable of treating the appropriate chamber with pacing stimulation including cardiac resynchronisation therapy.

The cardiac stimulator 10 has a housing 40, often referred to as the "can" or "case electrode". The housing 40 may function as a return electrode in "unipolar" modes. Further, the housing 40 includes connector (not shown) having a plurality of terminals (not shown) for connection with electrodes and/or sensors.

The cardiac stimulator 10 includes a programmable microcontroller or control module 41 that inter alia controls the various modes of stimulation therapy. As well known within the art, the microcontroller 41 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 41 includes the ability to process or monitor input signals (data or information) as controlled by a program stored in a designated block of memory. The type of microcontroller is not critical to the described implementations. Rather, any suitable microcontroller 41 may be used that carries out the functions described herein. The use of micro-processor based control circuits for performing timing and data analysis are well known in the art.

Furthermore, the cardiac stimulator 10 includes a pacing module 42 adapted to provide pacing signals for delivery to the patient. The pacing module 42 comprises an atrial pulse generator 43 and a ventricular pulse generator 44 that generate pacing stimulation pulses for delivery by the leads 8 via an electrode configuration switch 45. It is understood that in order to provide stimulation therapy in each of the four chambers, the atrial and ventricular pulse generators 43 and 44, may include dedicated, independent pulse generators, multiplexed pulse generators, or shared pulse generators. The pulse generators 43 and 44 are controlled by the microcontroller 41 via appropriate control signals to trigger or inhibit stimulation pulses.

The microcontroller 41 further includes timing control circuitry 46 to control timing of the stimulation pulses (e.g. pacing rate, AV delay, VV delay, etc.) as well as to keep track of timing of refractory periods blanking intervals, etc. which is well known in the art. In addition, the microcontroller 41 may include components such as e.g. an arrhythmia detector (not shown) and/or a heart signal morphology detector (not shown).

In embodiments of the present invention, an optimization module 48 is included in the cardiac stimulator 10, which optimization module 48 is adapted to optimize an AV and VV delay based on IEGM signals to determine recommended AV and VV delays. Preferably, the optimization module 48 employs QuickOpt™ Timing Cycle Optimization for IEGM based AV timing optimization and VV timing optimization.

A calculation module 62 configured to calculate an AV delay correction value as a difference between a recommended AV delay and a reference AV delay, and/or a VV delay correction value as a difference between a recommended VV delay and a reference VV delay may be included in the cardiac stimulator 10.

The aforementioned components may be implemented as part of the microcontroller 41, or as software/firmware instructions programmed into the device and executed on the microcontroller 41 during certain modes of operation. As discussed above with reference to FIG. 1, the optimization module 48, the calculation module 62, and the updating module 65 can alternatively be arranged in the extracorporeal programmer unit 20 instead of being arranged in the cardiac stimulator 10.

A sensing circuit 47 comprising atrial sensing circuits and ventricular sensing circuits may also be coupled to the leads 8 through the switch 45 for detecting the presence of cardiac activity in each of the four chambers of the heart. Accordingly, the atrial sensing circuits and ventricular sensing circuits 47 may include dedicated sense amplifiers, multiplexed amplifiers, or shared amplifiers.

The output from the atrial sensing circuits and ventricular sensing circuits 47 are connected to the microcontroller 41, which, in turn, is able to control the atrial sensing circuits and ventricular sensing circuits 47.

Furthermore, the microcontroller 41 is coupled to a memory 49 by a suitable data/address bus (not shown), wherein the programmable operating parameters used by the microcontroller 41 are stored and modified, as required, in order to customize the operation of the cardiac stimulator to the needs of a particular patient. Such operating parameters define, for example, pacing pulse amplitude, pulse duration, etc. Advantageously, the operating parameters may be non-invasively programmed into the memory 49 through a communication module 52 including, for example, a telemetry circuit for telemetric communication via communication link 53 with the programmer unit 20 or a diagnostic system analyzer. The telemetry circuit advantageously allows intracardiac electrograms and status information relating to the operation of the device 10 to be sent to the programmer unit 20 through an established communication link 53.

The cardiac stimulator 10 may further includes a physiologic sensor 56, commonly referred to as a "rate-responsive" sensor because it is typically used to adjust pacing stimulation rate according to the exercise state of the patient. While shown as being included within the stimulator 10, it is to be understood that the physiologic sensor 56 also may be external to the stimulator, yet still be implanted within or carried by the patient. Examples of physiologic sensors include sensors that, for example, sense respiration rate, or activity variance.

Moreover, the cardiac stimulator 10 additionally includes a battery 58 that provides operating power to all of the circuits shown in FIG. 2. Preferably, the stimulator 10 employs lithium or similar battery technology.

Figure 3:
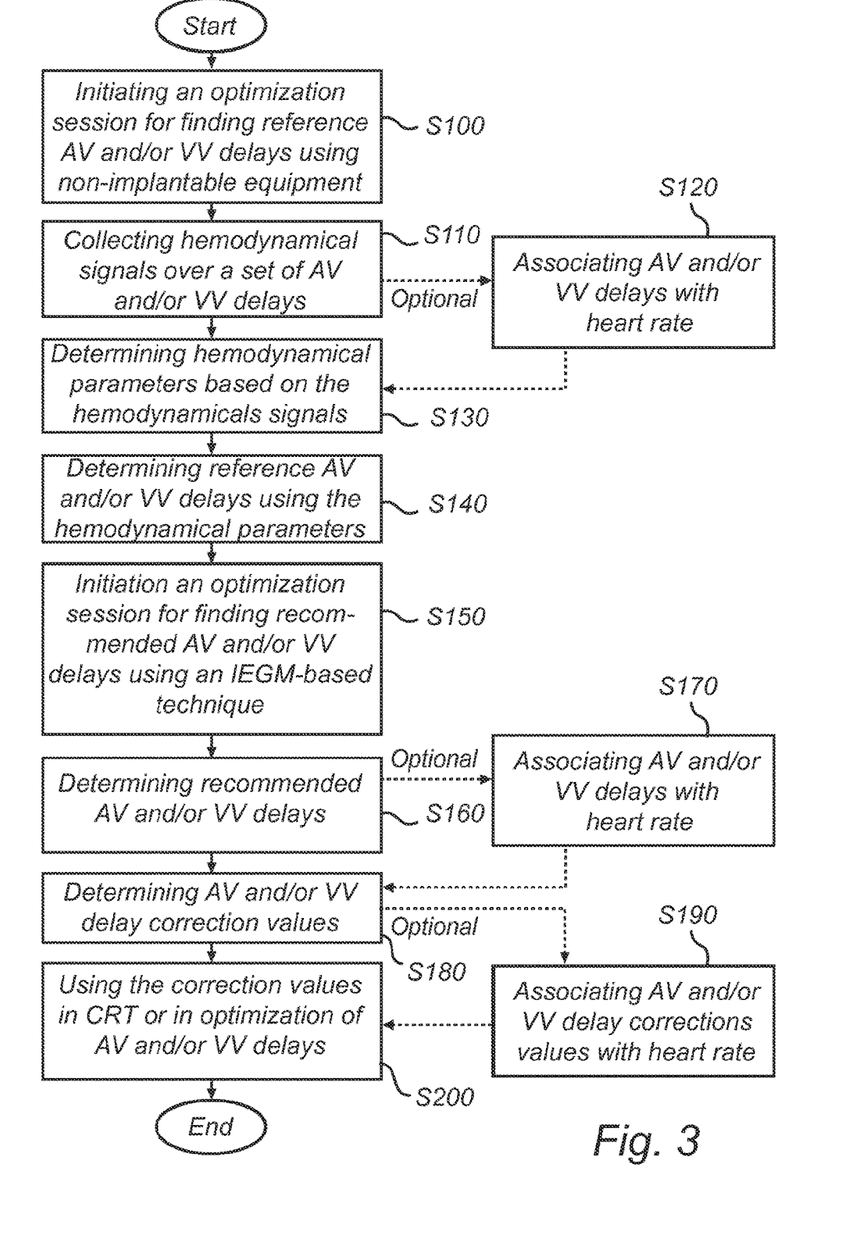
FIG. 3 is a flow chart illustrating steps of a method for optimizing AV and VV delays according to the present invention.

With reference now to FIG. 3, one embodiment of the method for optimizing timing data for CRT according to the present invention will be described.

First, at step S100, an external optimization of AV and/or VV delay for the patient 5 is initiated, which can be made automatically by the non-implantable equipment 30 or the programmer unit 20 or manually by the physician using the non-implantable equipment 30 or the programmer unit 20.

At step S110, hemodynamical signals are measured and collected using the non-implantable equipment 30, at least one hemodynamical signal is measured in the patient 5 using the non-implantable equipment 30. Preferably, a hemodynamical signal (or signals) is recorded during each AV delay and/or VV delay of a set of AV and/or VV delays.

Optionally, at step S120, the collected hemodynamical signals are associated with heart rate or a heart rate range during which the signals were obtained at.

Thereafter, at step S130, at least one hemodynamical parameter is determined based on the at least one hemodynamical signal and preferably at least one hemodynamical parameter is determined for each delay in the sweep (i.e. each delay in the set of AV and/or VV delay). Step S120 is optional and if not used, the algorithm proceeds directly to step S130 from step S110.

At step S140, optimal AV and/or VV delays, $AV_{ref}$ and/or $VV_{ref}$, are determined based on the hemodynamical signals and/or hemodynamical parameters in an optimization procedure. For example, if a non-invasive magnetic resonance imaging (MRI) technique is used to obtain the hemodynamical signals, ejection-fraction or stroke volume can be optimized to find the optimal AV and/or VV delay. In another alternative, if a Swan-Ganz catheter is used to monitoring cardiac output. Based on the measured cardiac output, stroke volume can be determined by dividing the cardiac output with heart rate. The stroke volume can then be used to optimize the AV and/or VV delays. Above, a number of alternative techniques have been described that can be used to obtain hemodynamical signals. These optimized AV and/or VV delays are now used as reference delays, $AV_{ref}$ and/or $VV_{ref}$, and are input to the programmer unit 20.

Subsequently, at step S150, a QuickOpt™ optimization session is initiated automatically by the cardiac stimulator 10 or the programmer unit 20 or manually by the physician using the programmer unit 20.

At step S160, recommended AV and/or VV delays, $AV_{QO}$ and/or $VV_{QO}$, are determined using the QuickOpt™ optimization algorithm.

Optional, at step S170, the recommended AV and/or VV delays are associated with a heart rate or heart rate range in which they were obtained. For example, one optimization session can be executed at a first heart rate range and a second session at a second range.

Step S170 is optional and if not used, the algorithm proceeds directly to step S180 from step S160.

It should be noted that the steps S100-S170 described above not necessarily have to be executed in the above given order but can be executed, for example, in an order such that step S150-S170 are performed first and steps S100-S140 subsequently.

Thereafter, at step S180, an AV delay correction value as a difference between a recommended AV delay and a reference AV delay, and/or a VV delay correction value as a difference between a recommended VV delay and a reference VV delay are calculated in accordance with the following:

$$\Delta_{AV} = AV_{QO} - AV_{Ref}$$

$$\Delta_{VV} = VV_{QO} - VV_{Ref}$$

The "delta" values, or corrections values, $\Delta_{AV}$ and/or $\Delta_{VV}$, are preferably calculated by the programmer unit 20 but may alternatively be calculated in the cardiac stimulator 10. In the latter alternative, the programmer unit 20 transmits the reference delays to the cardiac stimulator to enable the calculations. These correction values represent the difference in time (ms) between the recommended AV and/or VV delays and the reference AV and/or VV delays, respectively.

According to embodiments of the present invention, the correction values are labeled with the approximate heart rate, or heart rate range, during which they were obtained. Hence, in the optional step S190, the AV and/or VV delay correction value is/are associated with a heart rate or heart rate range.

At step S200, the AV and VV delay correction values are used in CRT or further optimization for update of AV and VV delays and/or subsequent correction values. This step may include programming the cardiac stimulator 10 with an AV and/or VV delay updated with correction values or with the reference delays obtained by means of the optimization performed by the non-implantable equipment 30.

Step S190 is optional and if not used, the algorithm proceeds directly to step S200 from step S180. If the correction values are associated with or labeled to the approximate heart rate or heart range during which they were obtained, it is possible to obtain rate dependent correction values and AV and VV delays. The AV and/or VV delay correction values may be binned together according to what approximate heart rate or heart rate range at which they were acquired. For example, if a first procedure to obtain AV and VV delay correction values were performed between 65-75 bpm, and a second procedure to obtain AV and VV delay correction values were performed between 75-85 bpm, the results from these procedures will not be mixed. Instead, this will result in two sets of correction values, one set of AV and VV delay correction values for the heart rate range between 65-75 bpm and one set of AV and VV delay correction values for the heart rate range between 75-85 bpm. Thus, it is possible to obtain heart rate specific correction values and, in turn, heart rate specific AV and VV delays.

The optimization procedure described above, i.e. an optimization procedure including an optimization session using non-implantable equipment for finding reference AV and/or VV delays and an IEGM-based optimization for finding recommended AV and/or VV delays, can be followed, after a predetermined period of time, by a further optimization procedure where the new correction values are used to redefine the present correction values, which is described below with reference to FIG. 5. The optimization procedure may also be followed by a new IEGM-based optimization for finding new recommended AV and/or VV delays which can be updated with the correction values. This is described below with reference to FIG. 4.

Figure 4:
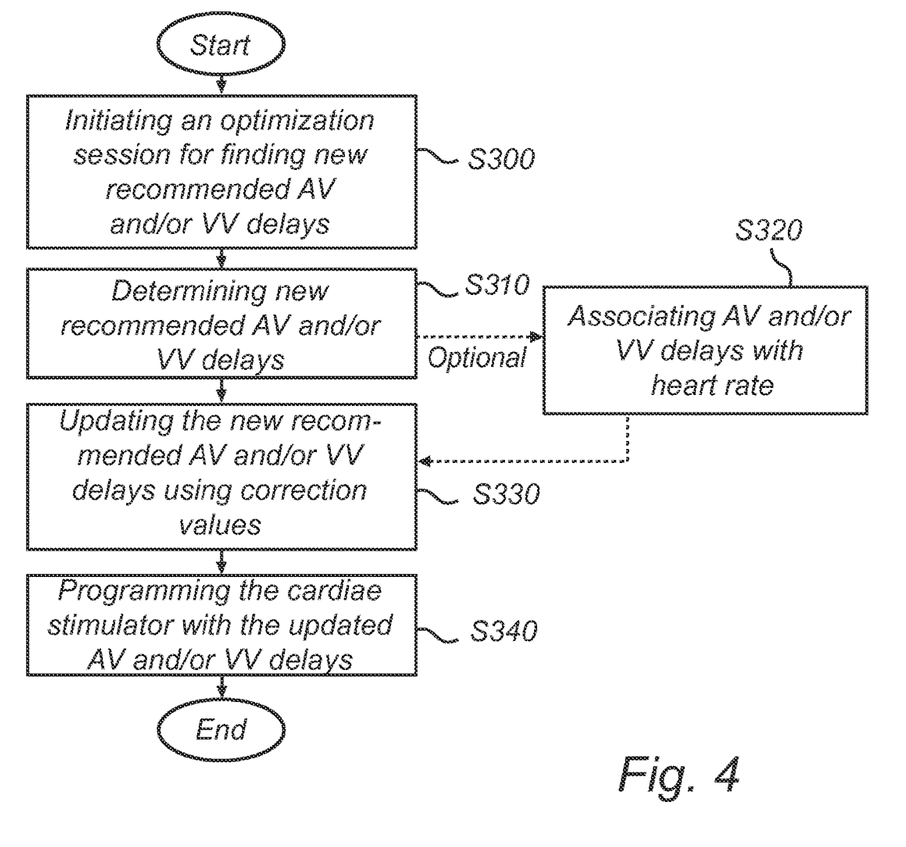
FIG. 4 is a flow chart illustrating steps of an embodiment of the method for optimizing AV and VV delays according to the present invention.

With reference now to FIG. 4, steps performed in an embodiment of the present invention will be described. This embodiment of the method is preferably performed a relatively short period of time, e.g. seven days, after optimization session including an optimization using the non-implantable equipment for obtaining reference delays.

At step S300, a new optimization session is initiated, by the physician at the clinic using the programmer unit 20, or automatically by the cardiac stimulator 10 for finding new recommended AV and/or VV delays using the QuickOpt™ optimization.

At step S310, a new set of recommended AV and/or VV delays, $AV_{QO-new}$ and/or $VV_{QO-new}$, is determined by carrying out the QuickOpt™ optimization procedure.

Optionally, at step S320, the new recommended AV and/or VV delays are associated with a heart rate or a heart rate range during which they were obtained. For example, several optimization sessions for finding AV and/or VV delays for different heart rates or different heart rate ranges are executed.

Thereafter, at step S330, the new recommended AV and/or VV delays, $AV_{QO-new}$ and/or $VV_{QO-new}$, are updated using the correction values, $\Delta_{AV}$ and/or $\Delta_{VV}$, to obtain updated recommended delays in accordance with the following:

$$AV_{QO-upd} = AV_{QO-new} - \Delta_{AV}; \text{ and}$$

$$VV_{QO-upd} = VV_{QO-new} - \Delta_{VV}.$$

Figure 5:
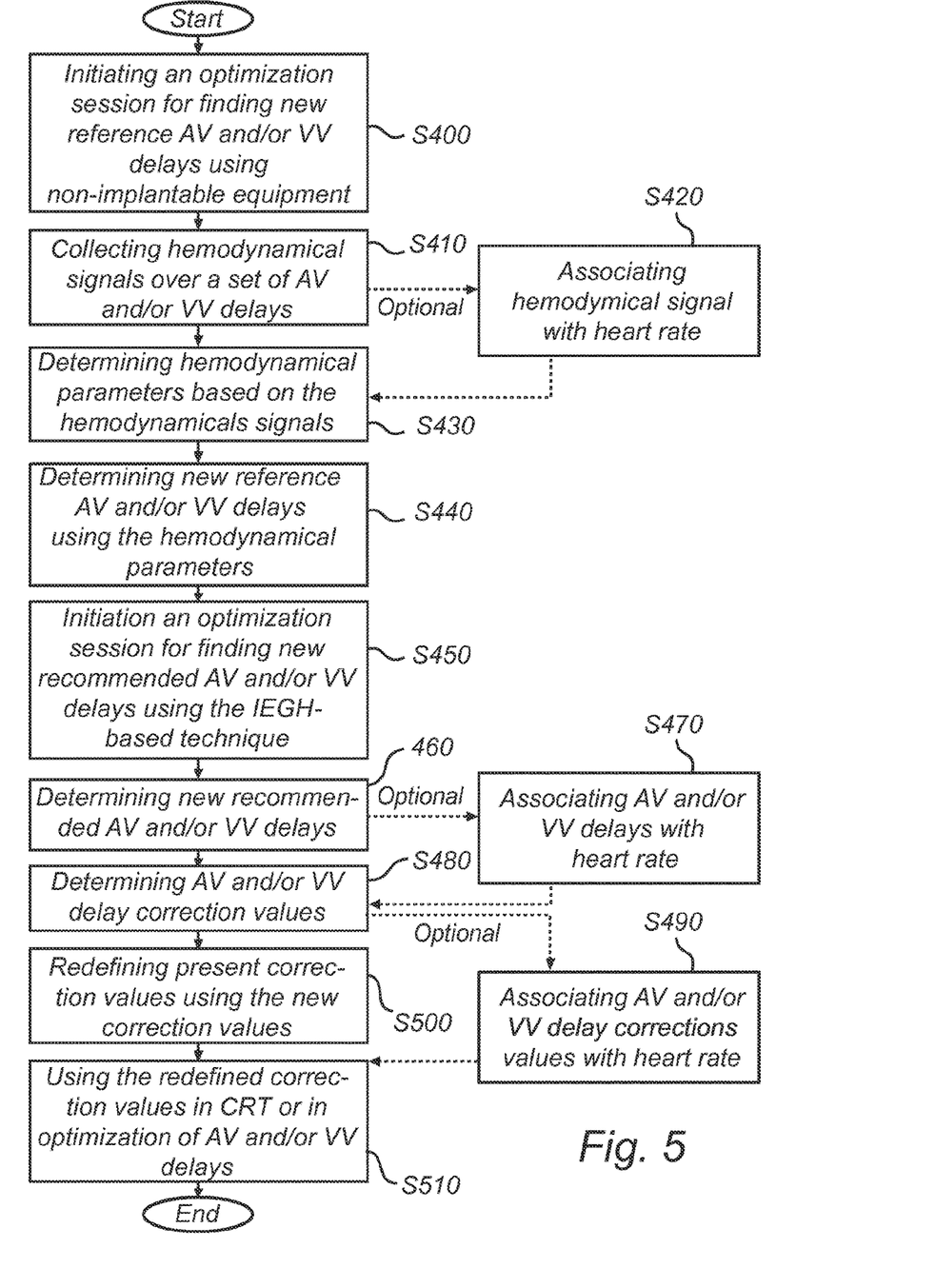
FIG. 5 is a flow chart illustrating steps of another embodiment of the method for optimizing AV and VV delays according to the present invention.

The correction values may be the corrections values from a preceding optimization procedure, or redefined correction values resulting from two or more optimization procedures (with reference to FIG. 5, it is described how the correction values are redefined).

Subsequently, at step S340, the cardiac stimulator 10 can be programmed with the updated AV and/or VV delays.

With reference to FIG. 5, steps performed in a further embodiment of the present invention will be described. Preferably, the following steps are performed in consecutive optimization procedures following an initial optimization session. The optimized AV and/VV delays are successively updated by successively redefined corrections values. The correction values will diminish and asymptotically approach a certain value, as the patient specific glitch between the electrically based recommendation (from the QuickOpt™ optimization) and the mechanically based recommendation (from the reference optimization using the non-implantable equipment) is identified and removed in an iterative manner.

At step S400, an external optimization of AV and/or VV delay for the patient 5 is initiated for finding new reference AV and/or VV delays, which can be made automatically by the non-implantable equipment 30 or the programmer unit 20 and manually by the physician using the non-implantable equipment 30 or the programmer unit 20.

At step S410, at least one hemodynamical signal is measured for the patient 5 and collected using the non-implantable equipment 30. Preferably, a hemodynamical signal (or signals) is recorded during each AV delay and/or VV delay of a set of AV and/or VV delays.

Optionally, at step S420, the at least one hemodynamical signal is associated with a heart rate or heart rate range during which the signal (-s) was/were obtained.

Thereafter, at step S430, at least one hemodynamical parameter is determined based on the at least one hemodynamical signal and preferably at least one hemodynamical parameter is determined for each delay in the sweep (i.e. each delay in the set of AV and/or VV delay).

At step S440, a new set of optimal AV and/or VV delays, $AV_{ref-new}$ and/or $VV_{ref-new}$, are determined based on the hemodynamical signals and/or hemodynamical parameters. These new reference AV and/or VV delays, $AV_{ref-new}$ and/or $VV_{ref-new}$, are input to the programmer unit 20.

Subsequently, at step S450, an QuickOpt™ optimization session is initiated for finding new recommended AV and/or VV delays, for example, manually by the physician via the programmer unit 20, or automatically by the cardiac stimulator 10 or by the programmer unit 20.

At step S460, the QuickOpt™ optimization session is performed to determine new recommended AV and/or VV delays. As discussed above, the cardiac stimulator 10 or the programmer unit 20 may perform the optimization procedure. The optimization procedure results in recommended new AV and/or VV delays, $AV_{QO-new}$ and/or $VV_{QO-new}$.

Optionally, at step S470, the new recommended AV and/or VV delays are associated with a heart rate or a heart rate range during which they were obtained. In one embodiment, several optimization sessions can be executed at different heart rates or heart rate ranges to find a set of AV and/or VV delays for each heart rate or heart rate range.

It should be noted that the steps S 400-S470 described above not necessarily have to be executed in the above given order but can be executed, for example, such that step S450-S470 are performed first and steps S400-S440 thereafter.

Thereafter, at step S480, new AV and/or VV delay correction values are determined as a difference between the new recommended AV delay and the new reference AV delay and the new recommended VV delay and the new reference VV, respectively, in accordance with the following:

$$\Delta_{AV-new} = AV_{QO-new} - AV_{Ref-new}$$

$$\Delta_{VV-new} = VV_{QO-new} - VV_{Ref-new}$$

The new "delta" values, or corrections values, $\Delta_{AV-new}$ and/or $\Delta_{VV-new}$, are preferably calculated by the programmer unit 20 but may alternatively be calculated in the cardiac stimulator 10. In the latter alternative, the programmer unit 20 has transmitted the reference delays to the cardiac stimulator to enable the calculations. These correction values represent the difference in time (ms) between the recommended AV and/or VV delays and the reference AV and/or VV delays, respectively.

According to embodiments of the present invention, the correction values are labeled with the approximate heart rate, or heart rate range, during which they were obtained. Hence, in the optional step S490, the AV and/or VV delay correction value is/are associated with a heart rate or heart rate range.

At step S500, the corrections values are redefined in accordance with the following:

$$\Delta_{AV-redef} = \Delta_{AV-old} + \Delta_{AV-new}$$

$$\Delta_{VV-redef} = \Delta_{VV-old} + \Delta_{VV-new}$$

wherein $\Delta_{AV-old}$ and $\Delta_{VV-old}$ are delta values from the preceding optimization session.

At step S510, the redefined AV and VV delay correction values are used in CRT or further optimization for update of the AV and VV delays. This step may include programming the cardiac stimulator 10 with an AV and/or VV delay updated with correction values as follows:

$$AV_{QO-upd} = AV_{QO-new} - \Delta_{redef}; \text{ and}$$

$$VV_{QO-upd} = VV_{QO-new} - \Delta_{redef}$$

Alternatively, the cardiac stimulator is programmed with the new reference delays.

At a subsequent optimization procedure where IEGM based AV and/or VV delays determined using the QuickOpt™, the steps S300-S340 described with reference to FIG. 4 can be repeated.

The correction values can be further redefined by repeating the steps S400-S500. Thereby, the optimized AV and/VV delays can also be successively updated using the successively redefined corrections values. The correction values will diminish and asymptotically approach a certain value, as the patient specific glitch between the electrically based recommendation (from the QuickOpt™ optimization) and the mechanically based recommendation (from the reference optimization using the non-implantable equipment) is identified and removed in an iterative manner.

Although certain embodiments and examples have been described herein, it will be understood by those skilled in the art that many aspects of the devices and methods shown and described in the present disclosure may be differently combined and/or modified to form still further embodiments. Alternative embodiments and/or uses of the devices and methods described above and obvious modifications and equivalents thereof are intended to be within the scope of the present disclosure. Thus, it is intended that the scope of the present invention should not be limited by the particular embodiments described above, but should be determined by a fair reading of the claims that follow.

The invention claim is:

1. A method for determining a delivery of cardiac pacing therapy using a cardiac stimulator and non-implantable equipment capable of measuring hemodynamical signals of a patient, the method comprising:
    determining recommended pacing settings including recommended atrio-ventricular pacing delays, AV delay and/or recommended interventricular pacing delays, VV delay, based only on IEGM data;
    measuring at least one hemodynamical signal of the patient using the non-implantable equipment;
    determining at least one hemodynamical parameter based on said at least one hemodynamical signal;
    determining reference pacing settings including reference atrio-ventricular pacing delays, AV delay and/or reference interventricular pacing delays, VV delay, based only on said hemodynamical parameters;
    calculating an AV delay correction value as a difference between a recommended AV delay and a reference AV delay, and/or a VV delay correction value as a difference between a recommended VV delay and a reference VV delay;
    wherein the AV delay correction is $\Delta_{AV}=AV_{IEGM}-AV_{Ref}$ and wherein the VV delays correction is $\Delta_{VV}=VV_{IEGM}-VV_{Ref}$; and
    using said AV and/or VV delay correction value in cardiac resynchronization therapy and/or optimization of AV and/or VV delay.

2. The method according to claim 1, wherein said step of using further comprises updating said recommended AV and/or VV delay with said AV and/or VV delay correction value, respectively, to obtain a updated recommended AV and/or VV delay.

3. The method according to claim 1, wherein said step of using further comprises redefining a set of new AV and/or VV delay correction values using at least one set of AV and W delay correction values obtained from a subsequent determination of AV and VV delay correction values.

4. The method according to claim 1, further comprising temporarily using reference AV and/or VV delays obtained in an optimization procedure, said procedure including an optimization session for finding reference AV and/or VV delays and an optimization session for finding recommended AV and/or VV delays, in pacing therapy during a period of time between said optimization procedure and a subsequent optimization procedure.

5. The method according to claim 1, wherein said non-implantable equipment is any one from the group including:
    non-invasive echocardiography/ultrasound equipment, non-invasive heart sound equipment, non-invasive photoplethysmography equipment for measurement using the fingers of the patient, and non-invasive magnetic resonance imaging (MRI) equipment.

6. The method according to claim 1, wherein said at least one hemodynamical parameter is one parameter, or combination of parameters, from the group including: stroke volume (SV), cardiac output (CO), ejection fraction (EF), trans mitral flow, septal to lateral wall activation delay, the first heart sound (S1), the second heart sound (S2), the energy of the first or second heart sound, LV $dP/dt_{max}$, pulmonary capillary wedge pressure, and/or left ventricular pressure.

7. A system including a cardiac stimulator, and non-implantable equipment capable of measuring hemodynamical signals of a patient, wherein said non-implantable equipment is configured to determine at least one hemodynamical parameter based on at least one measured hemodynamical signal said system further comprising:
    an optimization module configured to determine recommended pacing settings including recommended atrio-ventricular pacing delays, AV delay and/or recommended interventricular pacing delays, VV delay, based only on IEGM data;
    a reference setting determining module configured to determine reference pacing settings including reference atrio-ventricular pacing delays, AV delay and/or reference interventricular pacing delays, VV delay, based on said hemodynamical parameters;
    a calculation module configured to calculate an AV delay correction value as a difference between a recommended AV delay and a reference AV delay, and/or a VV delay correction value as a difference between a recommended VV delay and a reference VV delay, the AV delay correction value;
    wherein the AV delay correction is $\Delta_{AV}=AV_{IEGM}-AV_{Ref}$ and wherein the VV delay correction is $\Delta_{VV}=VV_{IEGM}-VV_{Ref}$; and
    an updating module configured to instruct a pacing module of cardiac stimulator to use said AV and/or VV delay correction value in cardiac resynchronization therapy and/or optimization of AV and/or VV delays.

8. The system according to claim 7, wherein said updating module is configured to update said recommended AV and/or VV delay with said AV and/or VV delay correction value, respectively, to obtain a updated recommended AV and/or VV delay.

9. The system according to claim 7, wherein said updating module is configured to redefine a set of new AV and/or VV delay correction values using at least one set of AV and VV delay correction values obtained from a subsequent determination of AV and VV delay correction values.

10. The system according to claim 7, wherein said pacing module is instructed to temporarily use reference AV and/or VV delays obtained in an optimization procedure, said procedure including an optimization session for finding reference AV and/or VV delays and an optimization session for finding recommended AV and/or VV delays, in pacing therapy during a period of time between said optimization procedure and a subsequent optimization procedure.

11. The system according to claim 7, wherein said non-implantable equipment is any one from the group including:

non-invasive echocardiography/ultrasound equipment, non-invasive heart sound equipment, non-invasive photoplethysmography equipment for measurement using the fingers of the patient, and non-invasive magnetic resonance imaging (MRI) equipment.

12. The system according to claim 7, wherein said at least one hemodynamical parameter is one parameter, or combination of parameters, from the group including: stroke volume (SV), cardiac output (CO), ejection fraction (EF), trans mitral flow, septa to lateral wall activation delay, the first heart sound (S1), the second heart sound (S2), the energy of the first or second heart sound, LV $dP/dt_{max}$, pulmonary capillary wedge pressure, and/or left ventricular pressure.

13. The system according to claim 7, further comprising an extracorporeal programmer unit.

14. The system according to claim 13, wherein said calculation module is arranged in said programmer unit or said cardiac stimulator.

15. The system according to claim 13, wherein said optimization module is arranged in said programmer unit or said cardiac stimulator.

16. The system according to claim 13, wherein said reference setting determining module is arranged in said programmer unit or in said non-implantable equipment.

17. The system according to claim 13, wherein said updating module is arranged in said programmer unit or said cardiac stimulator.

* * * * *